United States Patent [19]

Saito et al.

[11] Patent Number: 5,118,442
[45] Date of Patent: Jun. 2, 1992

[54] OPTICALLY ACTIVE COMPOUND

[75] Inventors: Masaki Saito; Makoto Takeda, both of Ibaraki; Noriko Wada, Ibarki; Shiroh Inui, Ibaraki; Hiroshi Taniguchi; Kazuaki Isomura, both of Fukuoka; Nobuyoshi Maruyama, Tokyo; Shoichi Seo, Ibaraki; Hiroshi Iwane, Ibaraki; Shin Kawano, Ibaraki, all of Japan

[73] Assignee: Mitsubishi Petrochemical Co., Ltd., Tokyo, Japan

[21] Appl. No.: 541,772

[22] Filed: Jun. 21, 1990

[30] Foreign Application Priority Data

Jun. 23, 1989 [JP] Japan .................................. 1-161065
Aug. 31, 1989 [JP] Japan .................................. 1-225198

[51] Int. Cl.$^5$ ..................... C09K 19/34; C09K 19/52; C07D 239/02; C07D 211/78
[52] U.S. Cl. ........................... 252/299.61; 252/299.01; 252/299.67; 544/298; 544/335; 544/336; 544/406; 544/408; 546/314; 546/315; 546/318; 546/322; 546/326; 546/325
[58] Field of Search ................. 252/299.01, 299.61, 252/299.67; 359/104; 544/298, 335; 560/59, 65, 73, 102, 108, 109; 546/314, 315, 318, 322, 326, 335, 339, 341

[56] References Cited

U.S. PATENT DOCUMENTS

| | | | |
|---|---|---|---|
| 4,973,426 | 11/1990 | Ohro et al. | 252/299.66 |
| 4,980,082 | 12/1990 | Ohba et al. | 252/299.61 |
| 4,985,172 | 1/1991 | Wingen et al. | 252/299.67 |
| 5,047,172 | 9/1991 | Saito et al. | 252/299.01 |
| 5,059,345 | 10/1991 | Kobagashi et al. | 252/299.61 |
| 5,064,568 | 11/1991 | Terashima et al. | 252/299.61 |

FOREIGN PATENT DOCUMENTS

| | | |
|---|---|---|
| 62-149669 | 7/1987 | Japan . |
| 63-307837 | 12/1988 | Japan . |
| WO8903416 | 4/1989 | PCT Int'l Appl. . |
| 2181429 | 4/1987 | United Kingdom . |

*Primary Examiner*—John S. Maples
*Assistant Examiner*—Shean C. Wu

*Attorney, Agent, or Firm*—Oblon, Spivak, McClelland, Maier & Neustadt

[57] ABSTRACT

An optically active compound represented by formula (I):

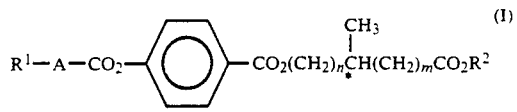

wherein $R^1$ represents an alkyl group having from 6 to 18 carbon atoms or an alkoxy group having from 6 to 18 carbon atoms; A represents

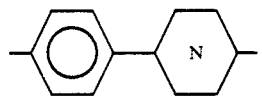

or

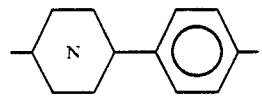

wherein ring

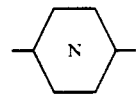

represents a nitrogen-containing hetero-aromatic ring; n and m each represents 0 or 1; $R^2$ represents an alkyl group having from 1 to 12 carbon atoms; and C* is an asymmetric carbon atom. The compound of formula (I) exhibits excellent physicochemical stability, a low temperature range for the chiral smectic C phase when used either alone or in combination with other compounds, and a rapid response.

10 Claims, No Drawings

OPTICALLY ACTIVE COMPOUND

FIELD OF THE INVENTION

This invention relates to a novel optically active compound useful as an electro-optical element material either as it is or as blended with other liquid crystal compounds.

BACKGROUND OF THE INVENTION

Liquid crystal display elements have been widely employed as various display elements because of their low-voltage driving properties, low-energy consumption, and capability of reduction in size and thickness.

Most of the currently industrialized display elements are of TN (twisted nematic) made using nematic liquid crystals However, the TN display mode is slow in response in the order of few milliseconds, and it has recently turned out that a more rapid response can be obtained by using ferroelectric smectic liquid crystals.

Ferroelectric smectic liquid crystals are compounds typically exemplified by a 4-(4-n-decyloxybenzylideneamino)cinnamic acid 2-methylbutyl ester (hereinafter abbreviated as DOBAMBC), which was developed by R.B. Meyer, et al. in 1975, and are characterized by ferroelectric properties in their chiral smectic C phase as described in *J. Physique*. Vol. 36, L-63 (1975).

The liquid crystal thin film cell of DOBAMBC was found to exhibit a rapid response in the order of microsecond as described in N.A. Clark, et. al., *Appl. Phys. Lett.*, Vol. 36, p. 899 (1980). With this as a momentum, the ferroelectric smectic liquid crystals have recently been attracting attention as materials promising for opto-electronics related elements, such as a photo printer head, a light Fourier transform element, and a light bulb, as well as display elements, such as a liquid crystal TV.

Since known ferroelectric liquid crystals, when used alone, find difficulty in obtaining a broad temperature range sufficient for practical use, they have been used as a blend of two or more thereof to broaden the temperature range in which a chiral smectic C phase is exhibited. Under the present situation, however, not only is limited the choice of ferroelectric liquid crystals themselves and compounding compounds which can be blended to that effect, but also the available blends of liquid crystals are still insufficient in performance for practical use.

On the other hand, the following compound is known as a phenyl ester of a phenyl nitrogen-containing hetero-aromatic carboxylic acid as disclosed in JP-A-62-149669 (the term "JP-A" as used herein means an "unexamined published Japanese patent application").

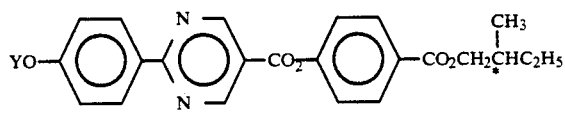

wherein Y represents an n-hexyl group, an n-octyl group, or an n-decyl group; and C* is an asymmetric carbon atom.

However, this compound has an extremely high temperature range for the chiral smectic C phase and is, therefore, difficult to apply to practical use.

SUMMARY OF THE INVENTION

An object of this invention is to eliminate the above-described problems associated with DOBAMBC or other several compounds so-far proposed and to provide a compound exhibiting excellent physicochemical stability, a low temperature range for the chiral smectic C phase when used either alone or in combination with other known optically active compounds, and a rapid response.

That is, the present invention relates to an optically active compound represented by formula (I):

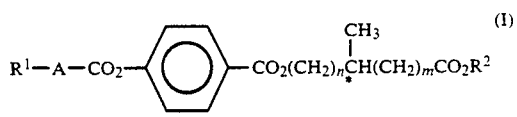

wherein $R^1$ represents an alkyl group having from 6 to 18 carbon atoms or an alkoxy group having from 6 to 18 carbon atoms; A represents

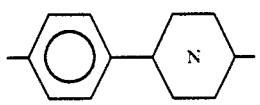

or

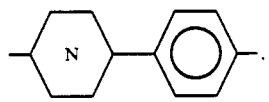

wherein ring

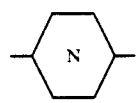

represents a nitrogen-containing hetero-aromatic ring; n and m each represents 0 or 1; $R^2$ represents an alkyl group having from 1 to 12 carbon atoms; and C* is an asymmetric carbon atom.

Unlike other liquid crystal compounds, e.g., DOBAMBC, the compound represented by formula (I) is physicochemically stable because of absence of a Schiff base and exhibits ferroelectric characteristics when used either alone or in combination with other known optically active compounds in a low temperature range for the chiral smectic C phase while showing a rapid response.

DETAILED DESCRIPTION OF THE INVENTION

The compound of formula (I) according to the present invention can be synthesized, for example, by reacting an optically active phenol compound represented by formula (II):

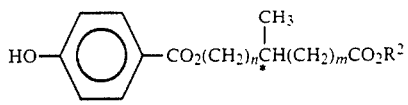 (II)

wherein n, m, $R^2$, and C* are as defined above, with a carboxylic acid represented by formula (III):

$$R^1-A-CO_2H \quad \text{(III)}$$

wherein $R^1$ and A are as defined above, or an acid chloride thereof.

The esterification reaction using the carboxylic acid of formula (III) can be carried out in a solvent, e.g., chloroform and methylene chloride, in the presence of a dehydrating agent, e.g., dicyclohexylcarbodiimide (hereinafter abbreviated as DCC), and a catalyst for activating a carboxylic acid, e.g., N,N-dimethyl-4-aminopyridine. The reaction is usually conducted at a temperature of from 0° to 100° C. for a period of from 1 to 24 hours.

The esterification reaction using the acid chloride of the carboxylic acid of formula (III) can be carried out in a solvent, e.g., hexane, toluene, and diethyl ether, in the presence of a basic substance, e.g., pyridine and triethylamine, as a dehydrochlorinating agent. The reaction is usually conducted at a temperature of from 0° to 130° C. for a period of from 1 to 24 hours.

The optically active phenol compound of formula (II) can be easily prepared, for example, by esterifying p-benzyloxybenzoic acid or p-benzyloxybenzoic chloride with an optically active alcohol compound represented by formula (IV):

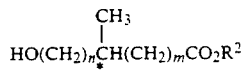 (IV)

wherein n, m, $R^2$, and C* are as defined above, and removing the benzyl ether group as a protective group by hydrogenolysis.

The compound of formula (III) can be synthesized by known processes. For example, the compound wherein ring

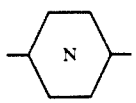

is a pyridine ring is disclosed in
ХИМИЯ · ТЕТЕРОЦИКЛИЧЕСКИХ · СОЕДИНЕНИЙ
888 (1980);
the compound wherein ring

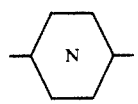

is a pyrimidine ring is disclosed in JP-B-55-6632 (the term "JP-B" as used herein means an "examined Japanese patent publication"); and the compound wherein ring

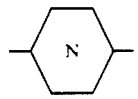

is a pyrazine ring is disclosed in *Nippon Kagakukai Shunki-Nenkai Koen Yokoshu*, 4IIB06 (1988).

Typical examples of the optically active compound of formula (I) are shown below.

(A) Compound wherein A is

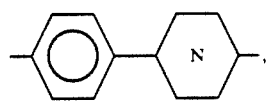

wherein ring

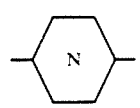

is a pyridine ring, a pyridazine ring, a pyrimidine ring, or a pyrazine ring; and n and m each is 0 or 1:

(A-a) Compounds wherein ring

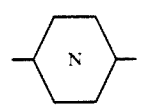

is a pyridine ring:
(1) 5-(4-Hexylphenyl)-2-pyridinecarboxylic acid (R)-4-[1-(methoxycarbonyl)ethoxycarbonyl]-phenyl ester
(2) 5-(4-Dodecyloxyphenyl)-2-pyridinecarboxylic acid (R)-4-[1-(methoxycarbonyl)ethoxycarbonyl]-phenyl ester
(3) 2-(4-Octadecylphenyl)-5-pyridinecarboxylic acid (S)-4-[(2-dodecyloxycarbonyl-1-methyl)-ethoxycarbonyl]phenyl ester (A-b) Compounds wherein ring

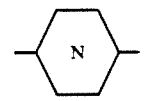

is a pyridazine ring:
(4) 3-[4-(9-Methyldecyl)phenyl]-6-pyridazine-carboxylic acid (S)-4-[2-(isopropoxycarbonyl)propoxycarbonyl]phenyl ester (A-c) Compounds wherein ring

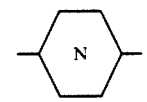

is a pyrimidine ring
(5) 2-(4-Hexyloxyphenyl)-5-pyrimidinecarboxylic acid (S)-4-[(3-t-butoxycarbonyl-2-methyl)-propoxycarbonyl]phenyl ester
(6) 2-(4-Dodecyloxyphenyl)-5-pyrimidinecarboxylic acid (R)-4-[1-(methoxycarbonyl)ethoxycarbonyl]phenyl ester
(7) 2-(4-Dodecyloxyphenyl)-5-pyrimidinecarboxylic acid (R)-4-[1-(ethoxycarbonyl)ethoxycarbonyl]phenyl ester
(8) 2-(4-Dodecyloxyphenyl)-5-pyrimidinecarboxylic acid (S)-4-[1-(isopropoxycarbonyl)-ethoxycarbonyl]phenyl ester
(9) 5-(4-Octadecyloxyphenyl)-2-pyrimidinecarboxylic acid (S)-4-[3-(3-methylbutoxycarbonyl)-2-methylpropoxycarbonyl]phenyl ester (A-d) Compounds wherein ring

is a pyrazine ring:
(10) 2-[4-(9-Methyldecyloxy)phenyl]-5-pyrazinecarboxylic acid (S)-4-[2-(3-methylbutoxycarbonyl)-propoxycarbonyl]-phenyl ester
(11) 2-(4-Dodecyloxyphenyl)-5-pyrazinecarboxylic acid (R)-4-[1-(methoxycarbonyl)-ethoxycarbonyl]-phenyl ester
(12) 2-(4-Dodecyloxyphenyl)-5-pyrazinecarboxylic acid (S)-4-[1-(ethoxycarbonyl)-ethoxycarbonyl]-phenyl ester
(13) 2-(4-Tridecylphenyl)-5-pyrazinecarboxylic acid (R)-4-[1-(methoxycarbonyl)-ethoxycarbonyl]phenyl ester
(14) 2-(4-Dodecyloxyphenyl)-5-pyrazinecarboxylic acid (R)-4-[(2-methoxycarbonyl-1-methyl)ethoxycarbonyl]phenyl ester
(15) 2-(4-Dodecyloxyphenyl)-5-pyrazinecarboxylic acid (R)-4-[(2-ethoxycarbonyl-1-methyl)ethoxycarbonyl]phenyl ester
(16) 2-(4-Tridecylphenyl)-5-pyrazinecarboxylic acid (R)-4-[(2-methoxycarbonyl-1-methyl)ethoxycarbonyl]phenyl ester
(17) 2-(4-Dodecyloxyphenyl)-5-pyrazinecarboxylic acid (S)-4-[2-(methoxycarbonyl)-propoxycarbonyl]phenyl ester (B) Compounds wherein A is

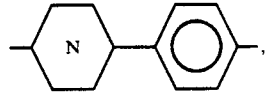

wherein ring

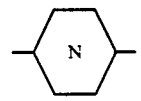

is a pyridine ring, a pyridazine ring, a pyrimidine ring or a pyrazine ring; and n and m each is 0 or 1:

(B-a) Compounds wherein ring

N is a pyridine ring:
(18) 4-[2-(9-Methyldecyloxy)pyridin-5-yl]-benzoic acid (R)-4-[(2-t-butoxycarbonyl-1-methyl)ethoxycarbonyl]phenyl ester
(19) 4-(5-Octadecyloxypyridin-2-yl)benzoic acid (R)-4-[1-(isopropoxycarbonyl)ethoxy-carbonyl]phenyl ester (B-b) Compounds wherein ring

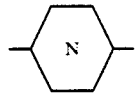

is a pyridazine ring:
(20) 4-(3-Hexyloxypyridazin-6-yl)benzoic acid (R)-4-[1-(dodecyloxycarbonyl)ethoxycarbonyl]phenyl ester (B-c) Compounds wherein ring

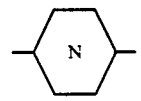

is a pyrimidine ring:
(21) 4-[5-(9-Methyldecyl)pyrimidin-2-yl]-benzoic acid (R)-4-[(2-methoxycarbonyl-1-methyl)ethoxycarbonyl]phenyl ester
(22) 4-(5-Dodecylpyrimidin-2-yl)benzoic acid (R)-4-[1-(methoxycarbonyl)ethoxycarbonyl]phenyl ester
(23) 4-(5-Dodecylpyrimidin-2-yl)benzoic acid (S)-4-[1-(ethoxycarbonyl)ethoxycarbonyl]-phenyl ester
(24) 4-(5-Dodecylpyrimidin-2-yl)benzoic acid (S)-4-[1-(butoxycarbonyl)ethoxycarbonyl]-phenyl ester
(25) 4-(5-Dodecylpyrimidin-2-yl)benzoic acid (S)-4-[1-(isopropoxycarbonyl)ethoxy carbonyl]phenyl ester
(26) 4-(5-Dodecylpyrimidin-2-yl)benzoic acid (R)-4-[(2-methoxycarbonyl-1-methyl)-ethoxycarbonyl]phenyl ester
(27) 4-(5-Dodecylpyrimidin-2-yl)benzoic acid (R)-4-[(2-ethoxycarbonyl-1-methyl)ethoxycarbonyl]phenyl ester
(28) 4-(5-Dodecylpyrimidin-2-yl)benzoic acid (S)-4-[(2-methoxycarbonyl)propoxycarbonyl]phenyl ester
(29) 4-(5-Tridecylpyrimidin-2-yl)benzoic acid (R)-4-[1-(methoxycarbonyl)ethoxycarbonyl]phenyl ester
(30) 4-(5-Tridecylpyrimidin-2-yl)benzoic acid (S)-4-[1-(ethoxycarbonyl)ethoxycarbonyl]phenyl ester
(31) 4-(5-Tridecylpyrimidin-2-yl)benzoic acid (S)-4-[1-(butoxycarbonyl)ethoxycarbonyl]phenyl ester
(32) 4-(5-Tridecylpyrimidin-2-yl)benzoic acid (S)-4-[1-(isopropoxycarbonyl)ethoxycarbonyl]phenyl ester
(33) 4-(5-Tridecylpyrimidin-2-yl)benzoic acid (R)-4-[(2-ethoxycarbonyl-1-methyl)ethoxycarbonyl]phenyl ester

(34) 4-(5-Tridecylpyrimidin-2-yl)benzoic acid (S)-4-[2-(methoxycarbonyl)propoxycarbonyl]phenyl ester

(35) 4-(5-Dodecyloxypyrimidin-2-yl)benzoic acid (R)-4-[1-(methoxycarbonyl)ethoxycarbonyl]phenyl ester

(36) 4-(5-Dodecyloxypyrimidin-2-yl)benzoic acid (S)-4-[1-(butoxycarbonyl)ethoxycarbonyl]phenyl ester

(37) 4-(5-Dodecyloxypyrimidin-2-yl)benzoic acid (S)-4-[1-(isopropoxycarbonyl)ethoxycarbonyl]phenyl ester

(38) 4-(5-Dodecyloxypyrimidin-2-yl)benzoic acid (R)-4-[(2-ethoxycarbonyl-1-methyl)ethoxycarbonyl]phenyl ester

(39) 4-(5-Dodecyloxypyrimidin-2-yl)benzoic acid (S)-4-[2-(methoxycarbonyl)propoxycarbonyl]phenyl ester

(40) 4-(2-Octadecylpyrimidin-5-yl)benzoic acid (S)-4-[2-(methoxycarbonyl)propoxycarbonyl]phenyl ester (B-d) Compounds wherein ring

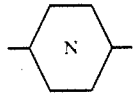

is a pyrazine ring:

(41) 4-(2-Hexylpyrazin-5-yl)benzoic acid (S)-4-[(3-dodecylcarbonyl-2-methyl)-propoxycarbonyl]phenyl ester

(42) 4-(2-Dodecyloxypyrazin-5-yl)benzoic acid (R)-4-[1-(methoxycarbonyl)ethoxycarbonyl]phenyl ester

(43) 4-(2-Dodecyloxypyrazin-5-yl)benzoic acid (S)-4-[1-(ethoxycarbonyl)ethoxycarbonyl]-phenyl ester

(44) 4-(2-Dodecyloxypyrazin-5-yl)benzoic acid (S)-4-[1-(butoxycarbonyl)ethoxycarbonyl]-phenyl ester

(45) 4-(2-Dodecyloxypyrazin-5-yl)benzoic acid (S)-4-[1-(isopropoxycarbonyl)ethoxycarbonyl]phenyl ester

(46) 4-(2-Dodecyloxypyrazin-5-yl)benzoic acid (R)-4-[(2-methoxycarbonyl-1-methyl)-ethoxycarbonyl]-phenyl ester

(47) 4-(2-Dodecyloxypyrazin-5-yl)benzoic acid (R)-4-[(2-ethoxycarbonyl-1-methyl)ethoxycarbonyl]phenyl ester Chemical structures of Compounds (1) to (47) enumerated above are shown in Table 1 below.

Of the compounds according to the present invention, preferred are those wherein $R^1$ is an alkyl or alkoxy group having 12 or 13 carbon atoms, and $R^2$ is an alkyl group having from 1 to 4 carbon atoms.

TABLE 1

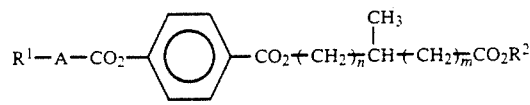

| Compound No. | $R^1$ | A | n | m | $R^2$ |
|---|---|---|---|---|---|
| (1) | $C_6H_{13}$ | (phenyl-pyridyl) | 0 | 0 | $CH_3$ |
| (2) | $C_{12}H_{25}O$ | " | " | " | " |
| (3) | $C_{18}H_{37}$ | (phenyl-pyridyl) | " | 1 | $C_{12}H_{25}$ |
| (4) | $CH_3CH(CH_2)_8$ with $CH_3$ | (phenyl-pyridazinyl) | 1 | 0 | $i$-$C_3H_7$ |
| (5) | $C_6H_{13}O$ | (phenyl-pyrimidinyl) | " | 1 | $t$-$C_4H_9$ |
| (6) | $C_{12}H_{25}O$ | (phenyl-pyrimidinyl) | 0 | 0 | $CH_3$ |
| (7) | " | " | " | " | $C_2H_5$ |
| (8) | " | " | " | " | $i$-$C_3H_7$ |

TABLE 1-continued $$R^1-A-CO_2-\phenyl-CO_2+CH_2\frac{}{n}\overset{CH_3}{\underset{|}{CH}}+CH_2\frac{}{m}CO_2R^2$$

| Compound No. | $R^1$ | A | n | m | $R^2$ |
|---|---|---|---|---|---|
| (9) | $C_{18}H_{37}O$ | 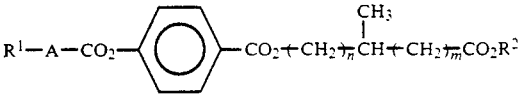 | 1 | 1 | $CH_3$<br>$CH_2CH_2\overset{|}{CH}CH_3$ |
| (10) | $CH_3CH(CH_2)_8O$ with $CH_3$ branch | 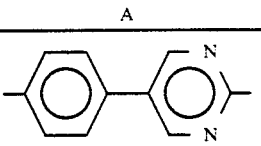 | " | 0 | " |
| (11) | $C_{12}H_{25}O$ | " | 0 | " | $CH_3$ |
| (12) | $C_{12}H_{25}O$ | 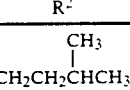 | 0 | 0 | $C_2H_5$ |
| (13) | $C_{13}H_{27}$ | " | " | " | $CH_3$ |
| (14) | $C_{12}H_{25}O$ | " | " | 1 | " |
| (15) | " | " | " | " | $C_2H_5$ |
| (16) | $C_{13}H_{27}$ | " | " | " | $CH_3$ |
| (17) | $C_{12}H_{25}O$ | " | 1 | 0 | " |
| (18) | $CH_3CH(CH_2)_8O$ with $CH_3$ branch | 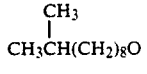 | 0 | 1 | t-$C_4H_9$ |
| (19) | $C_{18}H_{37}O$ | 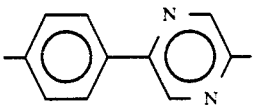 | " | 0 | i-$C_3H_7$ |
| (20) | $C_6H_{13}O$ | 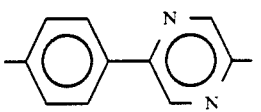 | " | " | $C_{12}H_{25}$ |
| (21) | $CH_3CH(CH_2)_8$ with $CH_3$ branch | 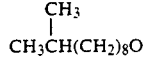 | " | 1 | $CH_3$ |
| (22) | $C_{12}H_{25}$ | " | " | 0 | " |
| (23) | " | " | " | " | $C_2H_5$ |
| (24) | $C_{12}H_{25}$ | 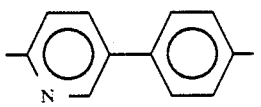 | 0 | 0 | $C_4H_9$ |
| (25) | " | " | " | " | i-$C_3H_7$ |
| (26) | " | " | " | 1 | $CH_3$ |
| (27) | " | " | " | " | $C_2H_5$ |
| (28) | " | " | 1 | 0 | $CH_3$ |
| (29) | $C_{13}H_{27}$ | " | 0 | " | " |
| (30) | $C_{13}H_{27}$ | 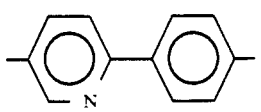 | 0 | 0 | $C_2H_5$ |
| (31) | " | " | " | " | $C_4H_9$ |
| (32) | " | " | " | " | i-$C_3H_7$ |

TABLE 1-continued

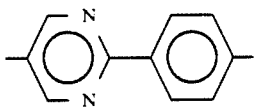

| Compound No. | R¹ | A | n | m | R² |
|---|---|---|---|---|---|
| (33) | " | " | " | 1 | $C_2H_5$ |
| (34) | " | " | 1 | 0 | $CH_3$ |
| (35) | $C_{12}H_{25}O$ | " | 0 | " | " |
| (36) | $C_{12}H_{25}O$ | 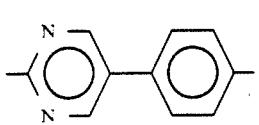 | 0 | 0 | $C_4H_9$ |
| (37) | " | " | " | " | $i\text{-}C_3H_7$ |
| (38) | " | " | " | 1 | $C_2H_5$ |
| (39) | " | " | 1 | 0 | $CH_3$ |
| (40) | $C_{18}H_{37}$ | 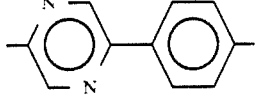 | " | " | " |
| (41) | $C_6H_{13}$ | 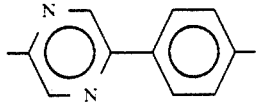 | " | 1 | $C_{12}H_{25}$ |
| (42) | $C_{12}H_{25}O$ | 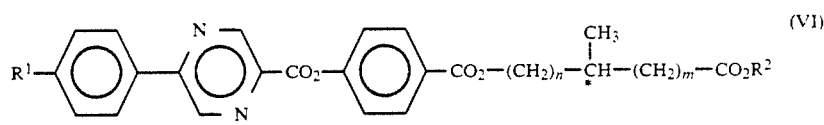 | 0 | 0 | $CH_3$ |
| (43) | " | " | " | " | $C_2H_5$ |
| (44) | " | " | " | " | $C_4H_9$ |
| (45) | " | " | " | " | $i\text{-}C_3H_7$ |
| (46) | " | " | " | 1 | $CH_3$ |
| (47) | " | " | " | " | $C_2H_5$ |

The preferred embodiments are as follows:

1. An optically active compound represented by formula (V):

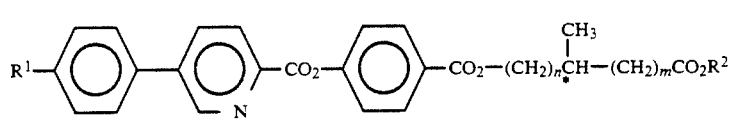

wherein $R^1$ represents an alkyl group having from 6 to 18 carbon atoms or an alkoxy group having from 6 to 18 carbon atoms, preferably, an alkoxy group having from 6 to 18 carbon atoms; $R^2$ represents an alkyl group having from 1 to 12 carbon atoms; n and m each represents 0 or 1; and C* is an asymmetric carbon atom.

2. An optically active compound represented by formula (VI):

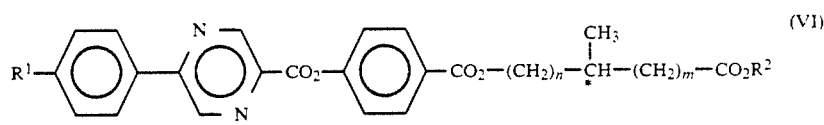

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

3. An optically active compound represented by formula (VII):

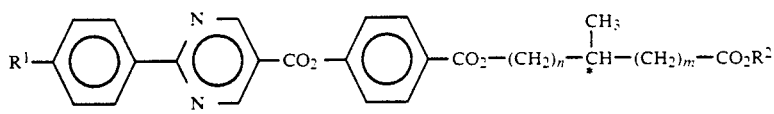 (VII)

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

4. An optically active compound represented by formula (VIII):

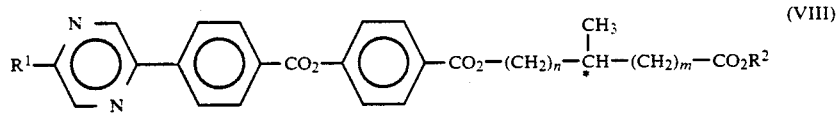 (VIII)

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

5. An optically active compound represented by formula (IX):

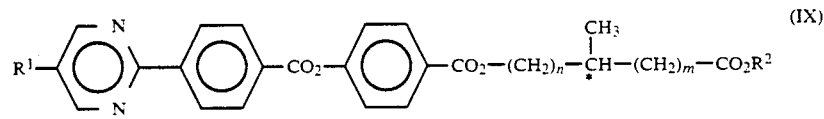 (IX)

wherein $R^1$ represents an alkyl group having from 6 to 18 carbon atoms or an alkoxy group having from 6 to 18 carbon atoms; $R^2$ represents an alkyl group having from to 12 carbon atoms; n and m each represents 0 or 1; and C* is an assymetric carbon atom.

6. A liquid crystal composition comprising at least one optically active compound represented by formula (I):

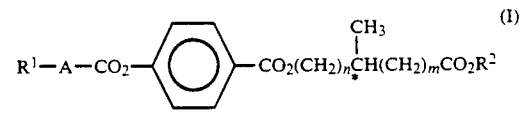 (I)

wherein $R^1$ represents an alkyl group having from 6 to 18 carbon atoms or an alkoxy group having from 6 to 18 carbon atoms; A represents

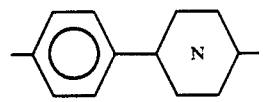

or

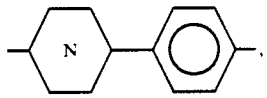, wherein ring

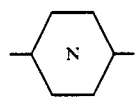

represents a nitrogen-containing hetero-aromatic ring; n and m each represents 0 or 1; $R^2$ represents an alkyl group having from 1 to 12 carbon atoms; and C is an asymmetric carbon atom.

Under the circumstances mentioned above, the optically active compound represented by formula (I) is preferably used in an amount of from 0.1 to 99% by weight, more preferably from 1 to 90% by weight, based on the weight of the resulting liquid crystal composition.

The optically active compound represented by formula (I) can be combined with, for example, an optically active compound as disclosed in *Liquid Crystal Device Handbook*, edited by Nippon Gakujutsu Shinkokai, Dai 142 Iinkai, published by Nikkan Kogyo Shinbunsha, (1989).

The optically active compound represented by formula (I) can be combined with, for example, a chiral compound represented by the following formula (a) or (b):

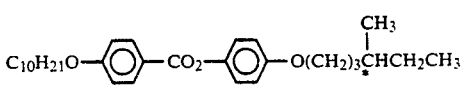

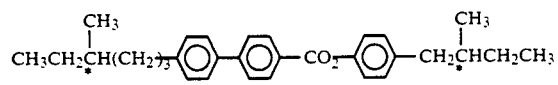

Further, the optically active compound represented by formula (I) can be combined with, for example, a compound which is not chiral itself and is represented by the following formula (c), (d), (e) or (f) to provide a composition which can be used as a ferroelectric liquid crystal.

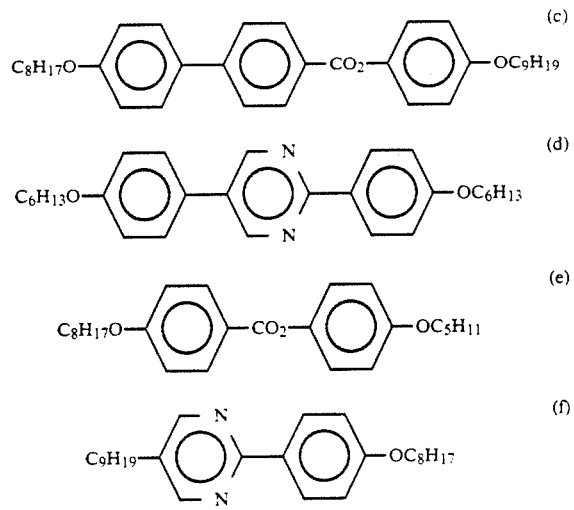

The present invention is now illustrated in greater detail with reference to Examples, but it should be understood that the present invention is not deemed to be limited thereto. All the percents are by weight unless otherwise indicated. Determination of the phase transition temperatures and identification of phases were conducted by means of a differential scanning calorimeter (DSC) and a polarizing microscope. "Cry" means a crystalline phase; "Sc*" a chiral smectic C phase; "$S_A$" a smectic A phase; "Ch" cholesteric phase; "Iso" an isotropic phase; and "X$_l$" (l is a natural number) an unassignable phase, respectively.

EXAMPLE 1

5-(4-Dodecyloxyphenyl)-2-pyridinecarboxylic Acid (R)-4-[1-(methoxycarbonyl)-ethoxycarbonyl]phenyl Ester (Compound (2))

1) Preparation of (R)-4-Benzyloxybenzoic Acid 1-(Methoxycarbonyl)ethyl Ester

In a 200 ml round flask were charged 4.57 g (20.0 mmol) of 4-benzyloxybenzoic acid, 2.29 g (22.0 mmol) of methyl (R)-lactate, 0.24 g (2.0 mmol) of N,N-dimethyl-4-aminopyridine, and 50 ml of methylene chloride, and the mixture was stirred at 25° C. To the mixture was added 4.54 g (22.0 mmol) cf DCC to conduct a reaction at 25° C. for 20 hours. After completion of the reaction, the solid was removed by filtration, and the filtrate was washed successively three times with 50 ml portions of water, three times with 50 ml portions of a 5% acetic acid aqueous solution, and finally three times with 50 ml portions of water. The organic solvent was removed under reduced pressure, and the residue was subjected to silica gel column chromatography using chloroform as an eluent to obtain 4.52 g (14.4 mmol) of the entitled compound in a yield of 72%. $^1$H-NMR (CDCl$_3$) δ (ppm): 1.60 (3H, d), 3.77 (3H, s), 5.10 (2H, s), 5.27 (1H, q), 6.97 (2H, d), 7.37 (5H, m), b 8.00 (2H, d).

IR (KBr disk) (cm$^{-1}$): 3100-2850, 1760, 1720, 1610, 1510, 1460, 1330, 1260, 1120, 850, 780, 740, 700.

2) Preparation of (R)-4-Hydroxybenzoic Acid 1-(Methoxycarbonyl)ethyl

In a 100 ml round flask equipped with a gas burette for introducing hydrogen were charged 3.14 g (10.0 mmol) of (R)-4-benzyloxybenzoic acid 1-(methoxycarbonyl)ethyl ester obtained in 1) above, 0.5 g of 5% palladium-on-carbon, and 20 ml of 100% acetic acid, followed by reacting at 25° C. for 5 hours in a hydrogen atmosphere. After completion of the reaction, the solid was removed by filtration, and the organic solvent was removed under reduced pressure. The residue was subjected to silica gel column chromatography using chloroform as an eluent to obtain 1.80 g (8.0 mmol) of the entitled compound in a yield of 80%. $^1$H-NMR (CDCl$_3$) δ (ppm): 1.63 (3H, d), 3.78 (3H, s), 5.30 (1H, q), 6.80 (2H, d), 7.90 (2H, d).

IR (NaCl) (cm$^{-1}$): 3380, 3030, 2990, 2950, 1760, 1715, 1610, 1595, 1515, 1450, 1270, 850, 815, 775, 700.

3) Preparation of Compound (2)

In a 50 ml round flask were charged 98.7 mg (0.44 mmol) of (R)-4-hydroxybenzoic acid 1-(methoxycarbonyl)ethyl ester obtained in 2) above, 153.4 mg (0.40 mmol) of 5-(4-dodecyloxyphenyl)-2-pyridinecarboxylic acid, 4.9 mg (0.04 mmol) of N,N-dimethyl-4-aminopyridine, and 5 ml of methylene chloride, followed by stirring at 25° C. To the mixture was added 90.8 mg (0.44 mmol) of DCC to conduct a reaction at 25° C. for 18 hours. After completion of the reaction, the solid was removed by filtration, and the filtrate was washed successively three times with 5 ml portions of water, three times with 5 ml portions of a 5% acetic acid aqueous solution, and finally three times with 5 ml portions of water. The organic solvent was removed under reduced pressure, and the residue was purified by silica gel column chromatography using chloroform as an eluent. Recrystallization from hexane gave 28.9 mg (0.049 mmol) of Compound (2) in a yield of 12% based on 5-(4-dodecyloxyphenyl)-2-pyridinecarboxylic acid.

$^1$H-NMR (CDCl$_3$) δ (ppm) 0.88 (3H, t), 1.18-1.42 (16H, m), 1.48 (2H, m), 1.64 (3H, d), 1.83 (2H, m), 3.79 (3H, s), 4.03 (2H, t), 5.36 (1H, q), 7.05 (2H, d), 7.39 (2H, d), 7.61 (2H, d), 8.05 (1H, dd), 8.19 (2H, d), 8.31 (1H, d), 9.03 (1H, d).

IR (KBr disk) (cm$^{-1}$): 2980, 2850, 2800, 1740, 1710, 1595, 1260, 1070, 825, 775, 755, 730, 710, 680.

Phase Transition Temperature (°C.)

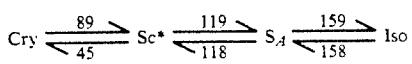

EXAMPLE 2

2-(4-Dodecyloxyphenyl)-5-pyrimidinecarboxylic Acid (R)-4-[1-(Methoxycarbonyl)-ethoxycarbonyl]phenyl Ester (Compound (6))

In the same manner as in Example 1-3), except for replacing 5-(4-dodecyloxyphenyl)-2-pyridinecarboxylic acid with 149.0 mg (0.40 mmol) of 2-(4-dodecyloxyphenyl)-5-pyrimidine, 141.6 mg (0.25 mmol) of Compound (6) was obtained in a yield of 61% based on 2-(4-dodecyloxyphenyl)-5-pyrimidinecarboxylic acid.

$^1$H-NMR (CDCl$_3$) δ (ppm): 0.88 (3H, t), 1.20–1.45 (16H, m), 1.52 (2H, m), 1.65 (3H, d), b 1.83 (2H, m), 3.79 (3H, s), 4.06 (2H, t), 5.37 (1H, q), 7.03 (2H, d), 7.37 (2H, d), 8.20 (2H, d), 8.52 (2H, d), 9.41 (2H, s).

IR (KBr disk) (cm$^{-1}$): 3000–2750, 1750, 1720, 1610, 1580, 1430, 1270, 1095, 855, 800, 770.

Phase Transition Temperature (°C.)

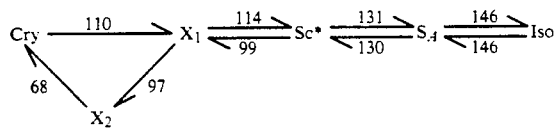

EXAMPLE 3

2-(4-Dodecyloxyphenyl)-5-pyrimidinecarboxylic Acid (S)-4-[1-(Ethoxycarbonyl)-ethoxycarbonyl]phenyl Ester (Compound (7))

1) In the same manner as in Example 1-1), except for replacing methyl (R)-lactate with ethyl (S)-lactate, (S)-4-benzyloxybenzoic acid 1-(ethoxycarbonyl)ethyl ester was obtained in a yield was 79%.

$^1$H-NMR (CDCl$_3$) δ (ppm): 1.26 (3H, t), 1.60 (3H, d), 4.21 (2H, q), 5.11 (2H, s), 5.26 (1H, q), 6.96 (2H, d), 7.37 (5H, m), 8.01 (2H, d).

IR (KBr disk) (cm$^{-1}$): 3050–2850, 1740, 1705, 1590, 1495, 1250, 1205, 1090, 850, 830, 760, 725, 685, 650.

2) In the same manner as in Example 1-2), except for using 10 mmol of (S)-4-benzyloxybenzoic acid 1-(ethoxycarbonyl)ethyl ester obtained in 1) above. The yield was 83%.

$^1$H-NMR (CDCl$_3$) δ (ppm): 1.30 (3H, t), 1.62 (3H, d), 4.23 (2H, q), 5.29 (1H, q), 6.82 (2H, d), 7.93 (2H, d), IR (NaCl) (cm$^{-1}$): 3380, 2990, 2950, 1750, 1740, 1720, 1610, 1595, 1515, 1275, 1220, 850, 815, 770, 750, 700.

3) Compound (7) was obtained in the same manner as in Example 1-3), except for using 0.44 mmol of (S)-4-hydroxybenzoic acid 1-(ethoxycarbonyl)ethyl ester prepared in 2) above. The yield was 69% based on 2-(4-dodecyloxyphenyl)-5-pyrimidinecarboxylic acid.

$^1$H-NMR (CDCl$_3$) δ (ppm): 0.88 (3H, t), 1.20–1.45 (19H, m), 1.52 (2H, m), 1.65 (3H, d), 1.83 (2H, m), 4.06 (2H, t), 4.25 (2H, q), 5.34 (1H, q), 7.03 (2H, d), 7.36 (2H, d), 8.20 (2H, d), 8.52 (2H, d), 9.41 (2H, s).

IR (KBr disk) (cm$^{-1}$): 3000–2750, 1755, 1715, 1600, 1570, 1425, 1380, 1250, 1200, 865, 840, 790, 760, 750.

Phase Transition Temperature (°C.)

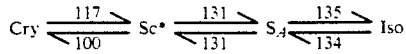

EXAMPLE 4

2-(4-Dodecyloxyphenyl)-5-pyrimidinecarboxylic Acid (S)-4-[1-(Isopropoxycarbonyl)-ethoxycarbonyl]phenyl Ester (Compound (8))

1) In the same manner as in Example 1-1), except for replacing methyl (R)-lactate with isopropyl (S)-lactate, (S)-4-benzyloxybenzoic acid 1-(isopropoxycarbonyl)ethyl ester was obtained in a yield of 48%.

$^1$H-NMR (CDCl$_3$) δ (ppm): 1.22 (3H, d), 1.25 (3H, d), 1.60 (3H, d), 5.06 (1H, m), 5.11 (2H, s), 5.27 (1H, q), 6.97 (2H, d), 7.37 (5H, m), 8.01 (2H, d).

IR (NaCl) (cm$^{-1}$): 3050–2850, 1760, 1720, 1610, 1510, 1455, 1330, 1260, 1120, 855, 785, 745, 705.

2) In the same manner as in Example 1-2), except for using 10 mmol of (S)-4-benzyloxybenzoic acid 1-(isopropoxycarbonyl)ethyl ester prepared in 1) above, (S)-4-hydroxybenzoic acid 1-(isopropoxycarbonyl)ethyl ester was obtained in a yield of 81%.

$^1$H-NMR (CDCl$_3$) δ (ppm) 1.23 (3H, d), 1.26 (3H, d), 1.60 (3H, d), 5.07 (1H, m), 5.22 (1H, q), 6.75 (2H, d), 7.87 (2H, d).

IR (KBr disk) (cm$^{-1}$): 3380, 3030, 2950, 1760, 1700, 1600, 1580, 1505, 1450, 1380, 1265, 1230, 1085, 840, 765, 750, 685.

In the same manner as in Example 1-3), except for using 0.44 mmol of (S)-4-hydroxybenzoic acid 1-(isopropoxycarbonyl)ethyl ester prepared in 2) above, Compound (8) was obtained in a yield of 64% based on 2-(4-dodecyloxyphenyl)-5-pyrimidinecarboxylic acid.

$^1$H-NMR (CDCl$_3$) δ (ppm): 0.88 (3H, t), 1.20–2.00 (29H, m), 1.63 (3H, d), 4.03 (2H, t), 5.07 (1H, m), 5.25 (1H, q), 6.97 (2H, d), 7.30 (2H, d), 8.13 (2H, d), 8.47 (2H, d), 9.33 (2H, s).

IR (KBr disk) (cm$^{-1}$): 3000–2750, 1750, 1720, 1605, 1575, 1500, 1430, 1250, 1205, 1155, 1085, 1015, 870, 840, 795, 765, 750.

Phase Transition Temperature (°C.)

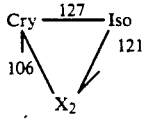

EXAMPLE 5

2-(4-Dodecyloxyphenyl)-5-pyrazinecarboxylic Acid (R)-4-[1-(Methoxycarbonyl)-ethoxycarbonyl]phenyl Ester (Compound (11))

In a 50 ml round flask were charged 86.3 mg (0.39 mmol) of (R)-4-hydroxybenzoic acid 1-(methoxycarbonyl)ethyl ester obtained in Example 1-2), 134.6 mg (0.35 mmol) of 2-(4-dodecyloxyphenyl)-5-pyrazinecarboxylic acid, 4.3 mg (0.035 mmol) of N,N-dimethyl-4-aminopyridine, and 5 ml of methylene chloride, followed by stirring at 25° C. To the mixture was added 79.4 mg (0.39 mmol) of DCC to conduct a reaction at 25° C. for 18 hours. After completion of the reaction, the reaction mixture was worked-up in the same manner as in Example 1-3) to obtain 27.6 mg (0.047 mmol) of Compound (11) in a yield of 13% based on 2-(4-dodecyloxyphenyl)-5-pyrazinecarboxylic acid.

$^1$H-NMR (CDCl$_3$) δ (ppm): 0.88 (3H, t), 1.20–1.40 (18H, m), 1.49 (3H, m), 1.65 (3H, d), 1.83 (2H, m), 3.79 (3H, s), 4.05 (2H, t), 5.36 (1H, q), 7.06 (2H, d), 7.40 (2H, d), 8.13 (2H, d), 8.21 (2H, d), 9.16 (1H, s), 9.41 (1H, s).

IR (KBr disk) (cm$^{-1}$): 3070, 2930, 2860, 1755, 1736, 1608, 1270, 1185, 1095, 895, 840, 800, 760.

MS (FAB) m/e (relative intensity): 591 (40, MH$^+$), 590 (10, M$^+$), 487 (10), 367 (100).

Phase Transition Temperature (°C.)

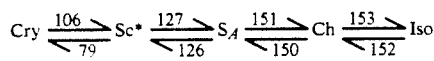

EXAMPLE 6

2-(4-Dodecyloxyphenyl)-5-pyrazinecarboxylic Acid (S)-4-[1-(Ethoxycarbonyl)-ethoxycarbonyl]phenyl Ester (Compound (12))

In the same manner as in Example 5, except for replacing (R)-hydroxybenzoic acid 1-(methoxycarbonyl)-ethyl ester with 0.39 mmol of (S)-4-hydroxybenzoic acid 1-(ethoxycarbonyl)ethyl ester which was prepared in the same manner as in Example 3-2), Compound (12) was obtained in a yield of 30% based on 2-(4-dodecyloxyphenyl)-5-pyrazinecarboxylic acid.

$^1$H-NMR (CDCl$_3$) δ (ppm): 0.88 (3H, t), 1.20–1.40 (19H, m), 1.49 (2H, m), 1.65 (3H, d), 1.82 (2H, m), 4.06 (2H, t), 4.25 (2H, q), 5.34 (1H, q), 7.06 (2H, d), 7.40 (2H, d), 8.13 (2H, d), 8.21 (2H, d), 9.16 (1H, s), 9.41 (1H, s).

IR (KBr disk) (cm$^{-1}$): 3070, 2930, 2860, 1765, 1755, 1733, 1610, 1510, 1470, 1270, 1190, 1100, 895, 840, 800, 755.

MS (FAB) m/e (relative intensity): 605 (60, MH$^+$), 604 (20, M$^+$), 487 (15), 367 (100).

Phase Transition Temperature (°C.)

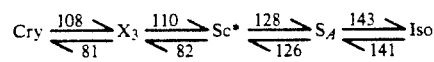

EXAMPLE 7

2-(4-Tridecylphenyl)-5-pyrazinecarboxylic Acid (R)-4-[1-(Methoxycarbonyl)-ethoxycarbonyl]phenyl Ester (Compound (13))

In the same manner as in Example 5, except for replacing 2-(4-dodecyloxyphenyl)-5-pyrazinecarboxylic acid with 2-(4-tridecylphenyl)-5-pyrazinecarboxylic acid, Compound (13) was prepared in a yield of 12% based on 2-(4-tridecylphenyl)-5-pyrazinecarboxylic acid.

$^1$H-NMR (CDCl$_3$) δ (ppm): 0.88 (3H, t), 1.20–1.45 (20H, m), 1.65 (3H, d), 1.65 (2H, m), 2.71 (2H, t), 3.79 (3H, s), 5.37 (1H, q), 7.39 (2H, d), 7.40 (2H, d), 8.07 (2H, d), 8.21 (2H, d), 9.21 (1H, s), 9.46 (1H, s).

IR (KBr disk) (cm$^{-1}$): 3080, 2930, 2860, 1750, 1720, 1605, 1525, 1510, 1475, 1420, 1275, 1170, 1110, 835, 795, 770, 720, 695.

MS (FAB) m/e (relative intensity): 589 (75, MH$^+$), 588 (10, M$^+$), 485 (40), 365 (100)

Phase Transition Temperature (°C.)

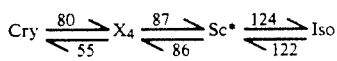

EXAMPLE 8

2-(4-Dodecyloxyphenyl)-5-pyrazinecarboxylic Acid (R)-4-[(2-Methoxycarbonyl-1-methyl)-ethoxycarbonyl]phenyl Ester (Compound (14))

1) Preparation of (R)-4-Benzyloxybenzoic Acid (2-Methoxycarbonyl-1-methyl)ethyl Ester:

In a 200 ml round flask were charged 6.85 g (30.0 mmol) of 4-benzyloxybenzoic acid, 3.90 g (33.0 mmol) of methyl (R)-3-hydroxybutyrate, 0.37 g (3.0 mmol) of N,N-dimethyl-4-aminopyridine, and 75 ml of methylene chloride, followed by stirring at 25° C. To the mixture was added 6.81 g (33.0 mmol) of DCC to conduct a reaction at 25° C. for 20 hours. After completion of the reaction, the solid was removed by filtration, and the filtrate was washed successively three times with 50 ml portions of water, three times with 50 ml portions of a 5% acetic acid aqueous solution, and finally three times with 50 ml portions of water. The organic solvent was removed under reduced pressure, and the residue was subjected to silica gel column chromatography using chloroform as an eluent to obtain 1.94 g (5.9 mmol) of the entitled compound in a yield of 20%. $^1$H-NMR (CDCl$_3$) δ (ppm): 1.37 (3H, d), 2.67 (2H, m), 3.60 (3H, s), 5.03 (2H, s), 5.42 (1H, 6.90 (2H, d), 7.30 (5H, s), 7.87 (2H, d).

IR (NaCl) (cm$^{-1}$): 3080, 3040, 2990, 2950, 1740, 1715, 1610, 1585, 1515, 1460, 1255, 1170, 915, 850, 770, 740, 700.

2) Preparation of (R)-4-Hydroxybenzoic Acid (2-Methoxycarbonyl-1-methyl)ethyl Ester:

In a 100 ml round flask equipped with a gas burette for introducing hydrogen were charged 1.94 g (5.9 mmol) of (R)-4-benzyloxybenzoic acid (2-methoxycarbonyl-1-methyl)ethyl ester obtained in 1) above, 0.3 g of 5% palladium-on-carbon, and 12 ml of 100% acetic acid, followed by reacting at 25° C. for 5 hours in a hydrogen atmosphere. After completion of the reaction, the solid was removed by filtration., and the organic solvent was removed under reduced pressure. The residue was subjected to silica gel column chromatography using chloroform as an eluent to obtain 1.05 g (4.6 mmol) of the entitled compound in a yield of 78%. $^1$H-NMR (CDCl$_3$) δ (ppm): 1.43 (3H, d), 2.65 (1H, dd), 2.80 (1H, dd), 3.69 (3H, s), 5.50 (1H, m), 6.85 (2H, d), 7.88 (2H, d).

IR (NaCl) (cm$^{-1}$): 3380, 3040, 3000, 2960, 1740, 1720, 1610, 1595, 1515, 1440, 1280, 1010, 930, 850, 775, 700.

3) Preparation of Compound (14)

In a 50 ml round flask were charged 126.9 mg (0.33 mmol) of 2-(4-dodecyloxyphenyl)-5-pyrazinecarboxylic acid and 431.9 mg (3.63 mmol) of thionyl chloride, and the mixture was refluxed for 2 hours. After the reaction, excess thionyl chloride was removed by distillation under reduced pressure. To the residue were added 2 ml of diethyl ether, 78.3 mg (0.99 mmol) of pyridine, and 86.5 mg (0.36 mmol) of (R)-4-hydroxybenzoic acid (2-methoxycarbonyl-1-methyl)ethyl ester obtained in 2) above to conduct a reaction at 25° C. for 19 hours. After completion of the reaction, 10 ml of methylene chloride was added to the reaction mixture, and the mixture was washed successively twice with 25 ml portions of water, twice with 25 ml portions of 0.5N hydrochloric acid aqueous solution, twice with 25 ml portions of a 0.5N sodium hydroxide aqueous solution, and finally twice with 25 ml portions of water. The organic solvent was removed under reduced pressure, and the residue was purified by silica gel column chromatography using a 20/1 (by volume) mixture of methylene chloride and diethyl ether as an eluent. Recrystallization from hexane gave 37.6 mg (0.062 mmol) of Compound (14) in a yield of 19% based on 2-(4-dodecyloxyphenyl)-5-pyrazinecarboxylic acid.

$^1$H-NMR (CDCl$_3$) δ (ppm): 0.83 (3H, t), 1.27 (16H, m), 1.46 (5H, m), 1.84 (2H, m), 2.66 (1H, dd), 2.82 (1H, dd), 3.70 (3H, s), 4.06 (2H, t), 5.53 (1H, m), 7.06 (2H, d), 7.37 (2H, d), 8.12 (2H, d), 8.13 (2H, d), 9.16 (1H, s), 9.41 (1H, s).

IR (KBr disk) (cm$^{-1}$): 3100, 2950, 2880, 1760, 1740, 1720, 1615, 1590, 1570, 1530, 1510, 1480, 1280, 1170, 1100, 890, 850, 805, 780, 760, 725, 695, 660, 635.

MS (FAB) m/e (relative intensity): 605 (80, MH$^+$), 604 (20, M$^+$), 487 (25), 367 (100).

Phase Transition Temperature (°C.):

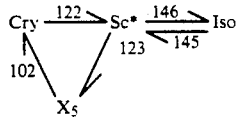

EXAMPLE 9

2-(4-Dodecyloxyphenyl)-5-pyrazinecarboxylic Acid (R)-4-[(2-Ethoxycarbonyl-1-methyl)-ethoxycarbonyl]-phenyl Ester (Compound (15))

In the same manner as in Example 8-1), except for replacing methyl (R)-3 hydroxybutyrate with ethyl (R)-3-hydroxybutyrate, (R)-4-benzyloxybenzoic acid (2-ethoxycarbonyl-1-methyl)ethyl ester was prepared in a yield of 19%.

$^1$H-NMR (CDCl$_3$) δ (ppm): 1.23 (3H, t), 1.45 (3H, d), 2.70 (2H, m), 4.13 (2H, q), 5.13 (2H, s), 5.50 (1H, m), 6.97 (2H, d), 7.43 (5H, s), 7.97 (2H, d).

IR (KBr disk) (cm$^{-1}$): 3080, 3040, 2990, 2950, 1740, 1715, 1610, 1580, 1510, 1255, 920, 850, 770, 740, 700.

MS (FAB) m/e (relative intensity): 343 (40, MH$^+$), 342 (15, M$^+$), 211 (100).

2) In the same manner as in Example 8-2), except for using 5.6 mmol of (R)-4-benzyloxybenzoic acid (2-ethoxycarbonyl-1-methyl)ethyl ester obtained in 1) above, (R)-4-hydroxybenzoic acid (2-ethoxycarbonyl-1-methyl)ethyl ester was obtained in a yield of 71%.

$^1$H-NMR (CDCl$_3$) δ (ppm): 1.21 (3H, t), 1.42 (2H, d), 2.67 (2H, m), 4.13 (2H, q), 5.48 (1H, m), 6.83 (2H, d), 7.90 (2H, d).

IR (NaCl) (cm$^{-1}$): 3370, 3050, 3000, 2950, 1740, 1715, 1610, 1595, 1520, 1280, 1170, 1100, 855, 775, 700.

3) In the same manner as in Example 8-3), except for using 0.36 mmol of (R)-4-hydroxybenzoic acid (2-ethoxycarbonyl-1-methyl)ethyl ester obtained in 2) above, Compound (15) was prepared in a yield of 22% based on 2-(4-dodecyloxyphenyl)-5-pyrazinecarboxylic acid.

$^1$H-NMR (CDCl$_3$) δ (ppm): 0.88 (3H, t), 1.20–1.45 (19H, m), 1.45–1.60 (5H, m), 1.83 (2H, m), 2.65 (1H, dd), 2.80 (1H, dd), 4.06 (2H, t), 4.15 (2H, q), 5.54 (1H, m), 7.06 (2H, d), 7.37 (2H, d), 8.12 (2H, d), 8.14 (2H, d), 9.16 (1H, s), 9.41 (1H, s).

IR (KBr disk) (cm$^{-1}$): 3100, 3070, 2920, 2850, 1750, 1735, 1710, 1605, 1580, 1560, 1520, 1470, 1270, 1165, 1090, 920, 885, 840, 795, 775, 755, 720, 690.

MS (EI) m/e (relative intensity): 618 (10, M$^+$), 367, (100).

Phase Transition Temperature (°C.)

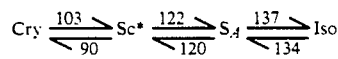

EXAMPLE 10

2-(4-Tridecylphenyl)-5-pyrazinecarboxylic Acid (R)-4-[(2-Mthoxycarbonyl-1-methyl)ethoxycarbonyl]-phenyl Ester (Compound (16))

In a 50 ml round flask were charged 65.5 mg (0.28 mmol) of (R)-4-hydroxybenzoic acid (2-methoxy-carbonyl-1-methyl)ethyl ester obtained in Example 8-2), 95.6 mg (0.25 mmol) of 2-(4-tridecylphenyl)-5-pyrazinecarboxylic acid, 3.1 mg (0.025 mmol) of N,N-dimethyl-4-aminopyridine, and 20 ml of methylene chloride, and the mixture was stirred at 25° C. To the mixture was added 56.7 mg (0.28 mmol) of DCC to conduct a reaction at 25° C. for 18 hours. After completion of the reaction, the solid was removed by filtration, and the filtrate was washed successively three times with 10 ml portions of water, three times with 10 ml portions of a 5% acetic acid aqueous solution, and finally three times with 10 ml portions of water. The organic solvent was removed under reduced pressure, and the residue was purified by silica gel column chromatography using a 20:1 (by volume) mixture of methylene chloride and diethyl ether as an eluent. Recrystallization from hexane gave 17.6 mg (0.029 mmol) of Compound (16) in a yield of 12% based on 2-(4-tridecylphenyl)-5-pyrazinecarboxylic acid.

$^1$H-NMR (CDCl$_3$) δ (ppm): 0.88 (3H, t), 1.20–1.45 (20H, m), 1.48 (3H, d), 1.64 (2H, m), 2.66 (2H, dd), 2.71 (2H, t), 2.82 (2H, dd), 3.69 (3H, s), 5.53 (1H, m), 7.39 (2H, d), 7.40 (2H, d), 8.07 (2H, d), 8.21 (2H, d), 9.21 (1H, s), 9.46 (1H, s).

IR (KBr disk) (cm$^{-1}$): 3080, 2960, 2930, 2860, 1760, 1740, 1720, 1610, 1580, 1565, 1510, 1470, 1280, 1095, 930, 890, 840, 795, 780, 760, 720, 690.

MS (EI) m/e (relative intensity): 602 (10, M$^+$), 365 (100).

Phase Transition Temperature (°C.)

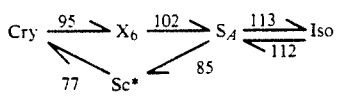

EXAMPLE 11

2-(4-Dodecyloxyphenyl)-5-pyrazinecarboxylic Acid (S)-4-[2-(Methoxycarbonyl)propoxycarbonyl]phenyl Ester (Compound (17))

1) Preparation of (S)-4-Benzyloxybenzoic acid (2-Methoxycarbonyl-2-methyl)ethyl Ester:

In a 200 ml round flask were charged 7.99 g (35.0 mmol) of 4-benzyloxybenzoic acid and 32.0 g (269 mmol) of thionyl chloride, and the mixture was refluxed for 2 hours. After the reaction, excess thionyl chloride was removed by distillation under reduced pressure. To the residue were added 40 ml of diethyl ether, 3.05 g (38.5 mmol) of pyridine, and 4.55 g (38.5 mmol) of methyl (S)-3-hydroxy-2-methylpropionate to conduct a reaction at 25° C. for 19 hours. After completion of the reaction, 50 ml of diethyl ether was added to the reaction mixture, and the mixture was washed successively once with 50 ml of water, once with 50 ml of a 2N sulfuric acid aqueous solution, once with 50 ml of a 0.5N sodium hydroxide aqueous solution, and finally once with 50 ml of water. The organic solvent was removed under reduced pressure, and the residue was subjected to silica gel column chromatography using chloroform as an eluent to obtain 9.92 g (30.2 mmol) of the entitled compound in a yield of 86%. $^1$H-NMR (CDCl$_3$) δ (ppm): 1.25 (3H, d), 2.90 (1H, m), 3.68 (3H, s), 4.40 (2H, d), 5.06 (2H, s), 6.92 (2H, d), 7.34 (5H, m), 7.88 (2H, d).

IR (NaCl) (cm$^{-1}$): 3080, 3040, 2990, 2960, 2890, 1740, 1720, 1610, 1580, 1510, 1455, 1255, 1170, 1105, 1010, 910, 850, 820, 770, 740, 700.

MS (EI) m/e (relative intensity): 328 (3, M$^+$), 297 (0.5), 211 (4), 91 (100).

2) Preparation of (S)-4-Hydroxybenzoic acid (2-Methoxycarbonyl-2-methyl)ethyl Ester:

In a 100 ml round flask equipped with a gas burette for introducing hydrogen were charged 9.90 g (30.0 mmol) of (S)-4-benzyloxybenzoic acid (2-methoxy-carbonyl-2-methyl)ethyl ester obtained in 1) above, 1.5 g of 5% palladium-on-carbon, and 60 ml of 100% acetic acid, followed by reacting at 25° C. for 5 hours in a hydrogen atmosphere. After completion of the reaction, the solid was removed by filtration, and the organic solvent was removed under reduced pressure. The residue was subjected to silica gel column chromatography using a 5:1 (by volume) mixture of chloroform and ethyl acetate as an eluent to obtain 5.54 g (23.3 mmol) of the entitled compound in a yield of 78%.

$^1$H-NMR (CDCl$_3$) δ (ppm): 1.30 (3H, d), 2.97 (1H, m), 3.73 (3H, s), 4.43 (2H, d), 6.90 (2H, d), 7.87 (2H, d).

IR (NaCl) (cm$^{-1}$): 3380, 3080, 3040, 2990, 2960, 1740, 1715, 1610, 1595, 1515, 1440, 1280, 1220, 990, 940, 910, 855, 770, 700.

MS (EI) m/e (relative intensity): 238 (20, M$^+$), 138 (80), 121 (100).

3) Preparation of Compound (17)

In a 50 ml round flask were charged 126.9 mg (0.33 mmol) of 2-(4-dodecyloxyphenyl)-5-pyrazinecarboxylic acid and 2.4 g (20 mmol) of thionyl chloride, followed by refluxing for 2 hours. After the reaction, excess thionyl chloride was removed by distillation under reduced pressure. To the residue were added 3 ml of toluene, 78.3 mg (0.99 mmol) of pyridine, and 82.6 mg (0.35 mmol) of (S)-4-hydroxybenzoic acid (2-methoxy-carbonyl-2-methyl)ethyl ester to conduct a reaction at 25° C. for 19 hours. After completion of the reaction, the reaction mixture was worked-up in the same manner as in Example 8-3) to obtain 39.6 mg (0.065 mmol) of Compound (17) in a yield of 20% based on 2-(4-dodecyloxyphenyl)-5-pyrazinecarboxylic acid.

$^1$H-NMR (CDCl$_3$) δ (ppm): 0.88 (3H, t), 1.15–1.45 (19H, m), 1.49 (2H, m), 1.83 (2H, m), 2.97 (1H, m), 3.74 (3H, s), 4.06 (2H, t), 4.48 (2H, m), 7.06 (2H, d), 7.38 (2H, d), 8.12 (2H, d), 8.12 (2H, d), 9.16 (1H, s), 9.41 (1H, s).

IR (KBr disk) (cm$^{-1}$): 3070, 2920, 2860, 1750, 1730, 1720, 1610, 1560, 1520, 1470, 1280, 920, 885, 840, 820, 800, 775, 760, 720, 690, 630.

MS (EI) m/e (relative intensity): 604 (5, M$^+$), 367 (60), 121 (100).

Phase Transition Temperature (°C.)

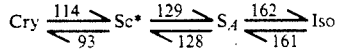

EXAMPLE 12

4-(5-Dodecylpyrimidin-2-yl)benzoic Acid (R)-4-[1-(Methoxycarbonyl)-ethoxycarbonyl]phenyl Ester (Compound (22))

In a 50 ml round flask were charged 86.3 mg (0.39 mmol) of (R)-4-hydroxybenzoic acid (1-methoxy-carbonyl)ethyl ester obtained in Example 1-2), 128.9 mg (0.35 mmol) of 4-(5-dodecylpyrimidin-2-yl)benzoic acid, 4.3 mg (0.035 mmol) of N,N-dimethyl-4-aminopyridine, and 20 ml of methylene chloride, followed by stirring at 25° C. To the mixture was added 79.4 mg (0.39 mmol) of DCC to conduct a reaction at 25° C. for 18 hours. After completion of the reaction, the solid was removed by filtration, and the filtrate was washed successively three times with 5 ml portions of water, three times with 5 ml portions of a 5% acetic acid aqueous solution, and finally three times with 5 ml portions of water. The organic solvent was removed under reduced pressure, and the residue was purified by silica gel column chromatography using a 20:1 (by volume) mixture of methylene chloride and diethyl ether as an eluent. Recrystallization from hexane gave 90.0 mg (0.16 mmol) of Compound (22) in a yield of 45% based on 4-(5-dodecylpyridmidin-2-yl) benzoic acid.

¹H-NMR (CDCl₃) δ (ppm): 0.88 (3H, t), 1.26–1.40 (18H, m), 1.64–1.70 (5H, m), 2.67 (2H, t), 3.79 (3H, s), 5.37 (1H, q), 7.36 (2H, d), 8.19 (2H, d), 8.32 (2H, d), 8.59 (2H, d), 8.69 (2H, s).

IR (KBr disk) (cm⁻¹): 3000-2850, 1785, 1720, 1605, 1595, 1430, 1270, 1080, 890, 870, 810, 770, 750, 700.

MS (EI) m/e (relative intensity): 574 (3, M+), 474 (30), 351 (100).

Phase Transition Temperature (°C.)

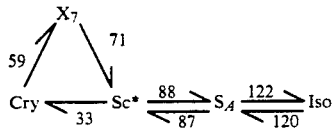

EXAMPLE 13

4-(5-Dodecylpyrimidin-2-yl)benzoic Acid (S)-4-[1-(Isopropoxycarbonyl)-ethoxycarbonyl]phenyl Ester (Compound (25))

In the same manner as in Example 12, except for replacing (R)-4-hydroxybenzoic acid 1-(methoxycarbonyl)-ethyl ester with 0.36 mmol of (S)-4-hydroxybenzoic acid 1-(isopropoxycarbonyl)ethyl ester which was prepared in the same manner as in Example 4-2), Compound (25) was obtained in a yield of 41% based on 4-(5-dodecylpyrimidin-2-yl)benzoic acid.

¹H-NMR (CDCl₃) δ (ppm): 0.88 (3H, t), 1.25–1.35 (24H, m), 1.62–1.70 (5H, m), 2.66 (2H, t), 5.10 (1H, m), 5.29 (1H, q), 7.36 (2H, d), 8.19 (2H, d), 8.32 (2H, d), 8.59 (2H, d), 8.69 (2H, s).

IR (KBr disk) (cm⁻¹): 3000-2870, 1740, 1730, 1605, 1580, 1430, 1280, 1080, 900, 870, 760.

MS (FAB) m/e (relative intensity): 603 (30, MH+), 471, (20), 351 (100).

Phase Transition Temperature (°C.)

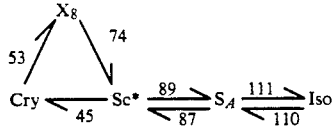

EXAMPLE 14

4-(5-Dodecylpyrimidin-2-yl)benzoic Acid (S)-4-[1-(Butoxycarbonyl)-ethoxycarbonyl]phenyl Ester (Compound (24))

1) In the same manner as in Example 1, except for replacing methyl (R)-lactate with butyl (S)-lactate, (S)-4-benzyloxybenzoic acid 1-(butoxycarbonyl)ethyl ester was obtained in a yield of 79%.

2) In the same manner as in Example 1-2), except for using (S)-4-benzyloxybenzoic acid 1-(butoxycarbonyl)ethyl ester obtained in 1) above, (S)-4-hydroxybenzoic acid 1-(butoxycarbonyl) ethyl ester was obtained in a yield of 84%.

¹H-NMR (CDCl₃) δ (ppm): 0.80–1.65 (10H, m), 4.18 (2H, t), 5.28 (1H, q), 6.75 (2H, d), 7.92 (2H, d).

IR (NaCl) (cm⁻¹): 3300, 3000-2900, 1720, 1605, 1280, 1220, 1170, 850, 780.

3) In the same manner as in Example 12, except for replacing (R)-4-hydroxybenzoic acid 1-(methoxycarbonyl)-ethyl ester with 0.36 mmol of (S)-4-hydroxybenzoic acid 1-(butoxycarbonyl)ethyl ester obtained in 2) above, Compound (24) was obtained in a yield of 69% based on 4-(5-dodecylpyrimidin-2-yl)benzoic acid.

¹H-NMR (CDCl₃) δ (ppm): 0.86–0.95 (6H, m), 1.26–1.43 (20H, m), 1.61–1.70 (7H, m), 2.67 (2H, d), 4.19 (2H, m), 5.34 (1H, q), 7.36 (2H, d), 8.19 (2H, d), 8.32 (2H, d), 8.59 (2H, d), 8.69 (2H, s).

IR (KBr disk) (cm⁻¹): 2980-2860, 1760, 1740, 1720, 1610, 1590, 1440, 1260, 1210, 900, 880, 760.

MS (EI) m/e (relative intensity): 616 (3, M+), 471 (10), 351 (100).

Phase Transition Temperature (°C.)

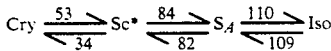

EXAMPLE 15

4-(5-Tridecylpyrimidin-2-yl)benzoic Acid (R)-4-[(2-Ethoxycarbonyl-1-methyl)-ethoxycarbonyl]phenyl Ester (Compound (33))

In the same manner as in Example 12, except for replacing (R)-4-hydroxybenzoic acid 1-(methoxycarbonyl)-ethyl ester with (R)-4-hydroxybenzoic acid (2-ethoxycarbonyl-1-methyl)ethyl ester which was prepared in the same manner as in Example 9-2) and replacing 4-(5-dodecylpyrimidin-2-yl)benzoic acid with 4-(5-tridecylpyrimidin-2-yl)benzoic acid, Compound (33) was obtained in a yield of 39% based on 4-(5-tridecylpyrimidin-2-yl)benzoic acid.

¹H-NMR (CDCl₃) δ (ppm): 0.88 (3H, d), 1.21–1.35 (23H, m), 1.45 (3H, d), 1.68 (2H, m), 2.62–2.83 (4H, m), 4.15 (2H, q), (1H, m), 7.33 (2H, d), 8.12 (2H, d), 8.31 (2H, d), 8.58, (2H, d), 8.69 (2H, s).

IR (KBr disk) (cm⁻¹): 2950-2800, 1710, 1700, 1600, 1570, 1430, 1250, 1110, 860, 790, 740.

MS (EI) m/e (relative intensity): 616 (0.2, M+), 485, (3), 365 (100).

Phase Transition Temperature (°C.)

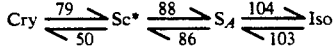

EXAMPLE 16

4-(5-Tridecylpyrimidin-2-yl)benzoic Acid (S)-4-[2-(methoxycarbonyl)-propoxycarbonyl]phenyl Ester (Compound (34))

In the same manner as in Example 12, except for replacing (R)-4-hydroxybenzoic acid 1-(methoxycarbonyl)-ethyl ester with (S)-4-hydroxybenzoic acid (2-methoxy-carbonyl-2-methyl)ethyl ester which was prepared in the same manner as in Example 11-2) and replacing 4-(5-dodecylpyrimidin-2-yl)benzoic acid with 4-(5-tridecylpyrimidin-2-yl)benzoic acid, Compound (34) was obtained in a yield of 59% based on 4-(5-tridecylpyrimidin-2-yl)benzoic acid.

$^1$H-NMR (CDCl$_3$) δ (ppm): 0.88 (3H, t), 1.26-1.35 (23H, m), 1.68 (2H, d), 2.67 (2H, t), 2.97 (1H, m), 3.74 (3H, s), 4.47 (2H, m), 7.34 (2H, d), 8.11 (2H, d), 8.31 (2H, d), 8.58 (2H, d), 8.69 (2H, s).

IR (KBr disk) (cm$^{-1}$): 2900-2800, 1730, 1600, 1430, 1250, 1080, 870, 750.

MS (FAB) m/e (relative intensity): 603 (40, MH$^+$), 485 (14), 365 (100).

Phase Transition Temperature (°C.)

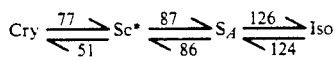

EXAMPLE 17

4-(5-Dodecyloxypyrimidin-2-yl)benzoic Acid (R)-4-[1-(Methoxycarbonyl)-ethoxycarbonyl]phenyl Ester (Compound (35))

In a 50 ml round flask were charged 191 mg (0.85 mmol) of (R)-4-hydroxybenzoic acid 1-(methoxycarbonyl)-ethyl ester as prepared in Example 1-2), 360 mg (0.935 mmol) of 4-(5-dodecyloxypyrimidin-2-yl)benzoic acid, 10.4 mg (0.085 mmol) of N,N-dimethyl-4-aminopyridine, and 20 ml of methylene chloride, followed by stirring at 25 ° C. To the mixture was added 193 mg (0.935 mmol) of DCC to conduct a reaction at 25° C. for 18 hours. After completion of the reaction, the solid was removed by filtration, and the filtrate was washed successively three times with 10 ml portions of water, three times with 10 ml portions of a 5% acetic acid aqueous solution, and three times with 10 ml portions of water. The organic solvent was removed under reduced pressure, and the residue was purified by silica gel column chromatography using a 20:1 (by volume) mixture of methylene chloride and diethyl ether. Recrystallization from hexane gave 110 mg (0.19 mmol) of Compound (35) in a yield of 22%.

$^1$H-NMR (CDCl$_3$) δ (ppm): 0.88 (3H, t), 1.2-1.6 (18H, m), 1.65 (3H, d), 1.86 (2H, m), 3.79 (3H, s), 4.14 (2H, t), 5.36 (1H, q), 7.37 (2H, d), 8.19 (2H, d), 8.29 (2H, d), 8.50 (2H, s), 8.51 (2H, d).

IR (KBr disk) (cm.$^{-1}$): 2900, 2850, 1760, 1720, 1600, 1570, 1435, 1270, 1115, 1070, 865, 750.

MS (EI) m/e (relative intensity): 590 (M$^+$, 0.1), 559, (1), 487 (2), 367 (100).

Phase Transition Temperature (°C.)

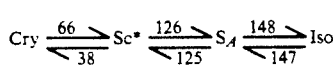

EXAMPLE 18

4-(5-Dodecyloxypyrimidin-2-yl)benzoic Acid (S)-4-[1-(Butoxycarbonyl)-ethoxycarbonyl]phenyl Ester (Compound (36))

In the same manner as in Example 17, except for replacing (R)-4-hydroxybenzoic acid 1-(methoxycarbonyl)ethyl ester with (S)-4-hydroxybenzoic acid 1-(butoxycarbonyl)ethyl ester which was prepared in the same manner as in Example 14-2), Compound (36) was obtained in a yield of 6.3%

$^1$H-NMR (CDCl$_3$) δ (ppm): 0.89 (3H, t), 0.93 (3H, t), 1.2-1.7 (25H, m), 1.86 (2H, m), 4.14 (2H, t), 4.19 (2H, t), 5.34 (1H, q), 7.36 (2H, d), 8.19 (2H, d), 8.29 (2H, d), 8.50 (2H, s), 8.51 (2H, d).

IR (KBr disk) (cm$^{-1}$): 2940, 2900, 2850, 2830, 755, 1740, 1730, 1715, 1595, 1570, 1540, 1500, 1435, 1355, 1270, 1200, 1110, 1055, 880, 865, 765, 750, 735.

MS (EI) m/e (relative intensity): 632 (M$^+$, 0.1), 487 (1), 367 (100).

Phase Transition Temperature (°C.)

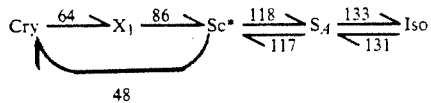

EXAMPLE 19

4-(5-Dodecyloxypyrimidin-2-yl)benzoic Acid (S)-4-[1-(Isopropoxycarbonyl)-ethoxycarbonyl]phenyl Ester (Compound (37))

In the same manner as in Example 17, except for replacing (R)-4-hydroxybenzoic acid 1-(methoxycarbonyl)-ethyl ester with (S)-4-hydroxybenzoic acid 1-(isopropoxycarbonyl)ethyl ester which was prepared in the same manner as in Example 4-2), Compound (37) was obtained in a yield of 8.3%.

$^1$H-NMR (CDCl$_3$) δ (ppm): 0.88 (3H, t), 1.2-1.6 (24H, m), 1.63 (3H, d), 1.85 (2H, m), 4.14 (2H, t), 5.10 (1H, sept), 5.29 (1H, q), 7.35 (2H, d), 8.19 (2H, d), 8.29 (2H, d), 8.50 (2H, s), 8.51 (2H, d).

IR (KBr disk) (cm$^{-1}$): 2900, 2840, 1750, 1720, 1600, 1570, 1535, 1500, 1430, 1385, 1270, 1205, 1105, 1065, 1010, 865, 750.

MS (EI) m/e (relative intensity): 618 (M$^+$, 0.1), 559 (1), 487 (2), 367 (100).

Phase Transition Temperature (°C.)

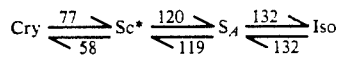

EXAMPLE 20

4-(5-Dodecyloxypyrimidin-2-yl)benzoic Acid (R)-4-[(2-Ethoxycarbonyl-1-methyl)-ethoxycarbonyl]phenyl Ester (Compound (38))

In the same manner as in Example 17, except for replacing (R)-4-hydroxybenzoic acid 1-(methoxycarbonyl)-ethyl ester with (R)-4-hydroxybenzoic acid (2-ethoxycarbonyl-1-methyl)ethyl ester which was prepared in the same manner as in Example 9-2), Compound (38) was obtained in a yield of 44%.

$^1$H-NMR (CDCl$_3$) δ (ppm): 0.88 (3H, t), 1.2-1.7 (24H, m), 1.86 (2H, m), 2.65 (1H, dd), 2.80 (1H, dd), 4.12 (2H, t), 4.14 (2H, q), 5.45 (1H, m), 7.34 (2H, d), 8.12 (2H, d), 8.29 (2H, d), 8.50 (2H, s), 8.51 (2H, d).

IR (KBr disk) (cm$^{-1}$): 2900, 2850, 1710, 1600, 1570, 1540, 1500, 1435, 1310, 1270, 1200, 1050, 1015, 1010, 910, 880, 865, 750.

MS (EI) m/e (relative intensity): 618 (M$^+$, 0.1), 367, (100).

Phase Transition Temperature (°C.)

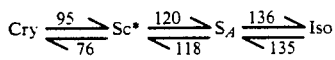

EXAMPLE 21

4-(5-Oodecyloxypyrimidin-2-yl)benzoic Acid (S)-4-[2-(Methoxycarbonyl)-propoxycarbonyl]phenyl Ester (Compound (39))

In the same manner as in Example 17, except for replacing (R)-4-hydroxybenzoic acid 1-(methoxycarbonyl)-ethyl ester with (S)-4-hydroxybenzoic acid 2-(methoxycarbonyl)propyl ester, Compound (39) was obtained in a yield of 38%.

$^1$H-NMR (CDCl$_3$) δ (ppm): 0.88 (3H, t), 1.2–1.6 (21H, m), 1.86 (2H, m), 2.98 (1H, m), 3.74 (3H, s), 4.14 (2H, t), 4.46 (2H, m), 7.35 (2H, d), 8.19 (2H, d), 8.29 (2H, d), 8.50 (2H, s), 8.51 (2H, d).

IR (KBr disk) (cm$^{-1}$): 2920, 2850, 1730, 1605, 1575, 1545, 1505, 1445, 1330, 1280, 1210, 1165, 1070, 1015, 870, 750, 690.

MS (EI) m/e (relative intensity): 605 (MH$^+$, 80), 604 (M$^+$, 5), 487 (30), 460 (25), 367 (100).

Phase Transition Temperature (°C.)

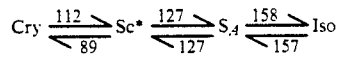

EXAMPLE 22

4-(2-Dodecyloxypyrazin-5-yl)benzoic Acid (R)-4-[1-(Methoxycarbonyl)-ethoxycarbonyl]phenyl Ester (Compound (42))

In a 50 ml round flask were charged 61.7 mg (0.28 mmol) of (R)-4-hydroxybenzoic acid (1-methoxycarbonyl)ethyl ester, 96.1 mg (0.25 mmol) of 4-(2-dodecyloxypyrazin-5-yl)benzoic acid, 3.1 mg (0.025 mmol) of N,N-dimethyl-4-aminopyridine, and 20 ml of methylene chloride, followed by stirring at 25° C. To the mixture was added 56.7 mg (0.28 mmol) of DCC to conduct a reaction at 25° C. for 18 hours. After completion of the reaction, the solid as removed by filtration, and the filtrate was washed successively three times with 10 ml portions of water, three times with 10 ml portions of a acetic acid aqueous solution, and three times with 10 ml portions of water. The organic solvent was removed under reduced pressure, and the residue was purified by silica gel column chromatography using a 20:1 (by volume) mixture of methylene chloride and diethyl ether as an eluent and then recrystallized from hexane to obtain 40.0 mg (0.070 mmol) of Compound (42) in a yield of 27% based on 4-(2-dodecyloxypyrazin-5-yl)benzoic acid.

$^1$H-NMR (CDCl$_3$) δ (ppm): 0.88 (3H, t), 1.20–1.55 (18H, m), 1.65 (3H, d), 1.81 (2H, tt), 3.79 (3H, s), 4.38 (2H, t), 5.37 (1H, q), 7.35 (2H, d), 8.09 (2H, d), 8.19 (2H, d), 8.30 (1H, s), 8.32 (1H, s), 8.60 (1H, s).

IR (KBr disk) (cm$^{-1}$): 2920, 2850, 1760, 1730, 1610, 1540, 1505, 1470, 1420, 1350, 1280, 1210, 1170, 1130, 1080, 1020, 860.

MS (EI) m/e (relative intensity): 590 (M$^+$, 0.4), 487 (1.8), 367 (100).

Phase Transition Temperature (°C.)

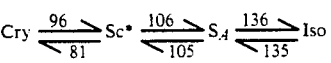

EXAMPLE 23

4-(2-Dodecyloxypyrazin-5-yl)benzoic Acid (S)-4-[1-(Ethoxycarbonyl)-ethoxycarbonyl]phenyl Ester (Compound (43))

In the same manner as in Example 22, except for replacing (R)-4-hydroxybenzoic acid (1-methoxycarbonyl)-ethyl ester with (S)-4-hydroxybenzoic acid (1-ethoxycarbonyl)ethyl ester which was prepared in the same manner as in Example 3-2), Compound (43) was obtained in a yield of 46%.

$^1$H-NMR (CDCl$_3$) δ (ppm): 0.88 (3H, t), 1.20–1.55 (21H, m), 1.65 (3H, d), 1.81 (2H, tt), 4.25 (2H, q), 4.38 (2H, t), 5.33 (1H, q), 7.34 (2H, d), 8.09 (2H, d), 8.19 (2H, d), 8.30 (2H, d), 8.32 (1H, s), 8.60 (1H, s).

IR (KBr disk) (cm$^{-1}$): 2910, 2850, 1750, 1730, 1605, 1540, 1500, 1465, 1420, 1270, 1205, 1170, 1120, 1080, 1020, 855.

MS (EI) m/e (relative intensity): 604 (M$^+$, 0.3), 487 (1.8), 367 (100).

Phase Transition Temperature (°C.)

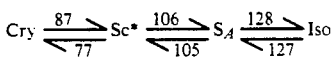

EXAMPLE 24

4-(2-Dodecyloxypyrazin-5-yl)benzoic Acid (S)-4-[1-(Butoxycarbonyl)-ethoxycarbonyl]phenyl Ester (Compound (44))

In the same manner as in Example 22, except for replacing (R)-4-hydroxybenzoic acid (1-methoxycarbonyl)-ethyl ester with (S)-4-hydroxybenzoic acid (1-butoxycarbonyl)ethyl ester which was prepared in the same manner as in Example 14-2), Compound (44) was obtained in a yield of 48%.

$^1$H-NMR (CDCl$_3$) δ (ppm): 0.88 (3H, t), 0.93 (3H, t), 1.20–1.53 (20H, m), 1.60–1.68 (5H, m), 1.82 (2H, tt), 4.19 (2H, m), 4.38 (2H, t), 5.34 (1H, q), 7.35 (2H, d), 8.09 (2H, d), 8.19 (2H, d), 8.30 (2H, d), 8.32 (1H, s), 8.60 , (1H, s).

IR (KBr disk) (cm$^{-1}$): 2900, 2850, 1760, 1730, 1720, 1605, 1540, 1500, 1470, 1420, 1270, 1205, 1165, 1120, 1080, 1010, 855. MS (EI) m/e (relative intensity): 632 (M$^+$, 1), 487 (2), 367 (100).

Phase Transition Temperature (°C.)

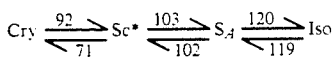

EXAMPLE 25

4-(2-Dodecyloxypyrazin-5-yl)benzoic Acid (S)-4-[1-(Isopropoxycarbonyl)-ethoxycarbonyl]phenyl Ester (Compound (45))

In the same manner as in Example 22, except for replacing (R)-4-hydroxybenzoic acid (1-methoxycarbonyl) ethyl ester with (S)-4-hydroxybenzoic acid (1-isopropoxycarbonyl)ethyl ester which was prepared in the same manner as in Example 4-2), Compound (45) was obtained in a yield of 30%.

$^1$H-NMR (CDCl$_3$) δ (ppm): 0.87 (3H, t), 1.17–1.52 (24H, m), 1.63 (3H, d), 1.81 (2H, tt), 4.38 (2H, t), 5.10 (1H, m), 5.28 (1H, q), 7.35 (2H, d), 8.09 (2H, d), 8.19 (2H, d), 8.30 (2H, d), 8.31 (1H, s), 8.60 (1H, s).

IR (KBr disk) (cm$^{-1}$): 2900, 2850, 1750, 1720, 1605, 1540, 1500, 1465, 1415, 1280, 1205, 1165, 1120, 1080, 1015, 1005, 855.

MS (EI) m/e (relative intensity): 618 (M$^+$, 1), 487 (2), 367 (100).

Phase Transition Temperature (°C.).

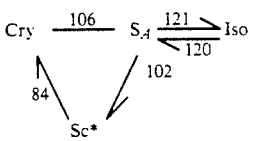

EXAMPLE 26

4-(2-Dodecyloxypyrazin-5-yl)benzoic Acid (R)-4-[(2-Methoxycarbonyl-1-methyl)-ethoxycarbonyl]phenyl Ester (Compound (46))

In the same manner as in Example 22, except for replacing (R)-4-hydroxybenzoic acid (1-methoxycarbonyl)-ethyl ester with (R)-4-hydroxybenzoic acid (2-methoxycarbonyl-1-methyl)ethyl ester which was prepared in the same manner as in Example 8-2), Compound (46) was obtained in a yield of 44%.

$^1$H-NMR (CDCl$_3$) δ (ppm): 0.88 (3H, t), 1.20–1.50 (21H, m), 1.83 (2H, tt), 2.66 (1H, dd), 2.82 (1H, dd), 3.69 (3H, s), 4.38 (2H, t), 5.53 (1H, m), 7.32 (2H, d), 8.10 (2H, d), 8.11 (2H, d), 8.29 (2H, d), 8.31 (1H, s), 8.60 (1H, s).

IR (KBr disk) (cm$^{-1}$): 2910, 2850, 1730, 1710, 1605, 1540, 1500, 1470, 1440, 1415, 1270, 1205, 1160, 1115, 1065, 1015, 880, 855.

Phase Transition Temperature (°C.)

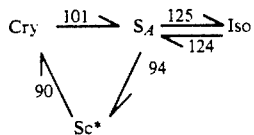

EXAMPLE 27

4-(2-Dodecyloxypyrazin-5-yl)benzoic Acid (R)-4-[(2-Ethoxycarbonyl-1-methyl)-ethoxycarbonyl]-phenyl Ester (Compound (47))

In the same manner as in Example 22, except for replacing (R)-4-hydroxybenzoic acid (1-methoxycarbonyl)ethyl ester with (R)-4-hydroxybenzoic acid (2-ethoxycarbonyl-1-methyl)ethyl which was prepared in the same manner as in Example 9-2), Compound (47) was obtained in a yield of 35%.

$^1$H-NMR (CDCl$_3$) δ (ppm): 0.88 (3H, t), 1.20–1.55 (24H, m), 1.83 (2H, tt), 2.65 (1H, dd), 2.80 (1H, dd), 4.15 (2H, q), 4.38 (2H, t), 5.54, (1H, m), 7.32 (2H, d), 8.10 (2H, d), 8.31 (1H, s), 8.60 (1H, s).

IR (KBr disk) (cm$^{-1}$): 2900, 2850, 1740, 1715, 1605, 1540, 1500, 1465, 1410, 1310, 1270, 1205, 1185, 1155, 1115, 1070, 1010, 855.

Phase Transition Temperature (°C.)

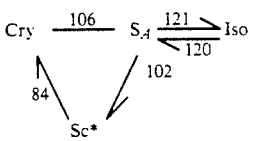

EXAMPLE 28

5-(4-Dodecyloxyphenyl)-2-pyridinecarboxylic acid (R)-4-[1-(methoxycarbonyl)ethoxycarbonyl]phenyl ester (Compound (2)) obtained in Example 1 was sealed into a liquid crystal cell having a cell thickness of about 4 μm, composed of a polyimide orientation film and an ITO (indium tin oxide) film as an electrode, and orientated by the action of an electromagnetic field to obtain a chiral smectic C phase of uniform mono-domain. An alternating electric field was applied thereto, and a response time was obtained as a reciprocal of a frequency at which the intensity of transmitted light became unable to follow the change of the electric field. As a result, a rapid response of 200 μs was obtained at 75° C. and 7.0 V.

EXAMPLE 29

2-(4-Dodecyloxyphenyl)-5-pyrimidinecarboxylic acid (R)-4-[1-(methoxycarbonyl)ethoxycarbonyl]phenyl ester (Compound (6)) obtained in Example 2 was sealed into a liquid crystal cell having a cell thickness of about 4 μm, composed of a polyimide orientation film and an ITO film as an electrode, and orientated by the action of an electromagnetic field to obtain a chiral smectic C phase of uniform mono-domain. An alternating electric field was applied thereto, and a response time was obtained as a reciprocal of a frequency at which the intensity of transmitted light became unable to follow the change of the electrical field. As a result, a rapid response of 25 μs was obtained at 122° C. and 7.5 V. The amount of spontaneous polarization was 60 nc/cm$^2$ at 100° C.

EXAMPLE 30

4-(5-Dodecyloxypyrimidin-2-yl)benzoic acid (R)-4-[1-(methoxycarbonyl)ethoxycarbonyl]phenyl ester (Compound (35)) obtained in Example 17 was sealed into a liquid crystal cell having a cell thickness of about 3 μm, composed of a polyimide orientation film and an ITO film as an electrode. The compound exhibiting an isotropic phase was gradually cooled to obtain a chiral smectic C phase of uniform mono-domain.

A response time was obtained from the peak of a polarization repulsion current on application of an alternating square wave of ±10 V. As a result, a rapid response of 16 μs was obtained at 107° C.

While the invention has been described in detail and with reference to specific embodiments thereof, it will be apparent to one skilled in the art that various changes and modifications can be made therein without departing from the spirit and scope thereof.

What is claimed is:

1. An optically active compound represented by formula (I):

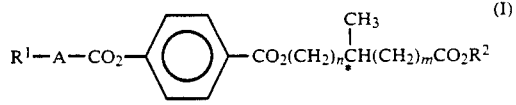

wherein $R^1$ represents an alkyl group having from 6 to 18 carbon atoms or an alkoxy group having from 6 to 18 carbon atoms; A represents

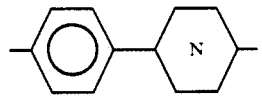

or

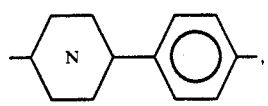

wherein ring

represents a nitrogen-containing hetero-aromatic ring; n and m each represents 0 or 1; $R^2$ represents an alkyl group having from 1 to 12 carbon atoms; and C* is an asymmetric carbon atom.

2. An optically active compound as claimed in claim 1, wherein ring

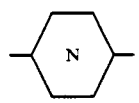

is a pyridine ring, a pyridazine ring, a pyrimidine ring, or a pyrazine ring.

3. An optically active compound as claimed in claim 1, wherein $R^1$ is an alkyl or alkoxy group having 12 or 13 carbon atoms, and $R^2$ is an alkyl group having from 1 to 4 carbon atoms.

4. An optically active compound represented by formula (V):

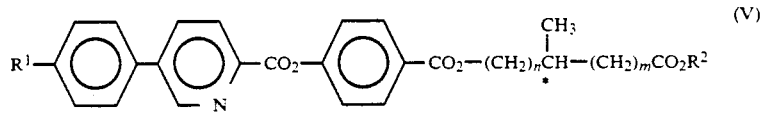

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an asymmetric carbon atom.

5. An optically active compound as claimed in claim 4, wherein $R^1$ is an alkoxy group having from 6 to 18 carbon atoms.

6. An optically active compound represented by formula (VI):

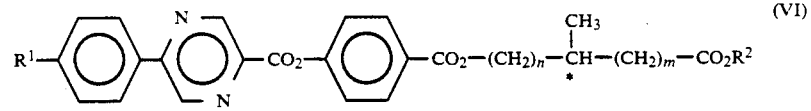

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

7. An optically active compound represented by formula (VII):

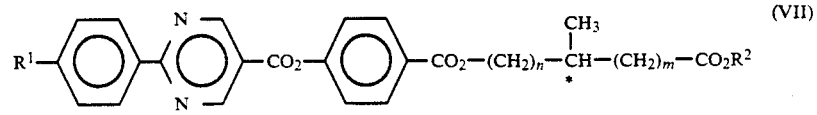

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

8. An optically active compound represented by formula (VIII):

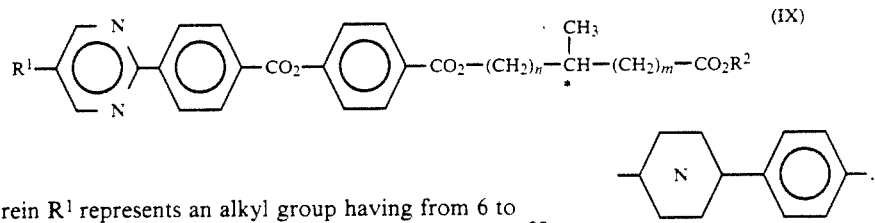

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

9. An optically active compound represented by formula (IX):

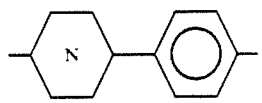

wherein $R^1$ represents an alkyl group having from 6 to 18 carbon atoms or an alkoxy group having from 6 to 18 carbon atoms; $R^2$ represents an alkyl group having from 1 to 12 carbon atoms; n and m each represents 0 or 1; and C* is an assymetric carbon atom.

10. A liquid crystal composition comprising at least one optically active compound represented by formula (I):

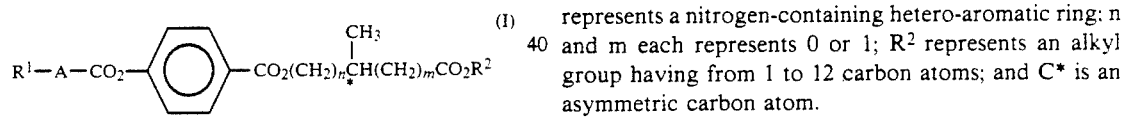

wherein $R^1$ represents an alkyl group having from 6 to 18 carbon atoms or an alkoxy group having from 6 to 18 carbon atoms; A represents

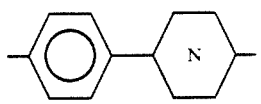

or

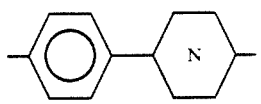

wherein ring

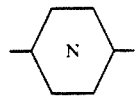

represents a nitrogen-containing hetero-aromatic ring; n and m each represents 0 or 1; $R^2$ represents an alkyl group having from 1 to 12 carbon atoms; and C* is an asymmetric carbon atom.

* * * * *